United States Patent [19]

Semm

[11] Patent Number: 4,830,002

[45] Date of Patent: May 16, 1989

[54] INSTRUMENT GRIP

[75] Inventor: Kurt Semm, Kiel, Fed. Rep. of Germany

[73] Assignee: Wisap, Gesellschaft Fur Wissenschaftlichen Apparatebau mbH, Sauerlach, Fed. Rep. of Germany

[21] Appl. No.: 93,581

[22] Filed: Sep. 4, 1987

[30] Foreign Application Priority Data

Sep. 4, 1986 [DE] Fed. Rep. of Germany ....... 3630210

[51] Int. Cl.$^4$ ............................................. A61B 17/28
[52] U.S. Cl. .................................. 128/321; 128/354; 81/489
[58] Field of Search ................... 128/303 R, 321–324, 128/352–353, 354, 356; 81/489

[56] References Cited

U.S. PATENT DOCUMENTS

| 1,168,115 | 1/1916 | Rueckert | 128/354 X |
| 4,163,446 | 8/1979 | Jamshidi | 128/754 |
| 4,393,872 | 7/1983 | Reznik et al. | 128/321 |

Primary Examiner—Dalton L. Truluck
Attorney, Agent, or Firm—Fleit, Jacobson, Cohn, & Price

[57] ABSTRACT

A relatively flat, disk-shaped gripping device for a medical instrument is moved axially with respect to the instrument by exerting pressure by the hand, or in a circumferential or rotary direction by the finger or thumb. The gripping device is fixed in non-rotary manner on the distal side of the shaft of a medical instrument, allowing a surgeon to easily place the instrument into any random rotary position by finger actuation, without adjusting the basic position of the hand.

18 Claims, 2 Drawing Sheets

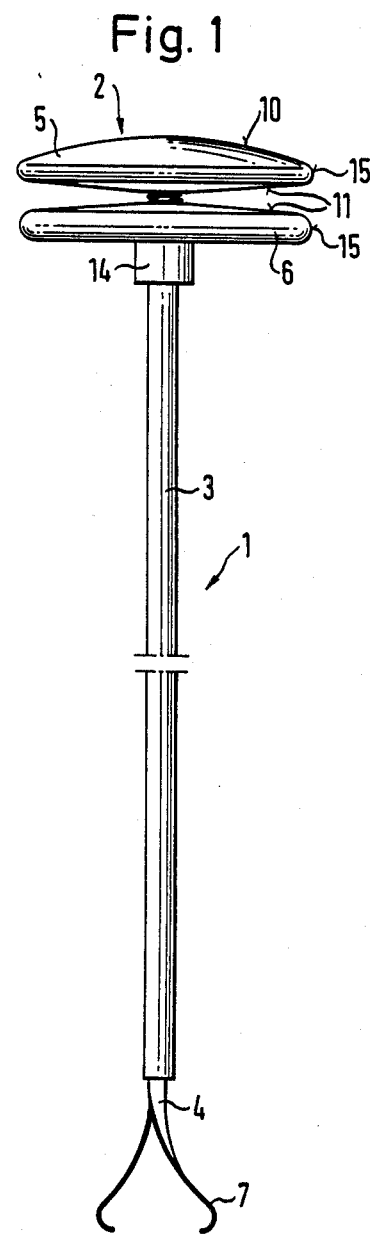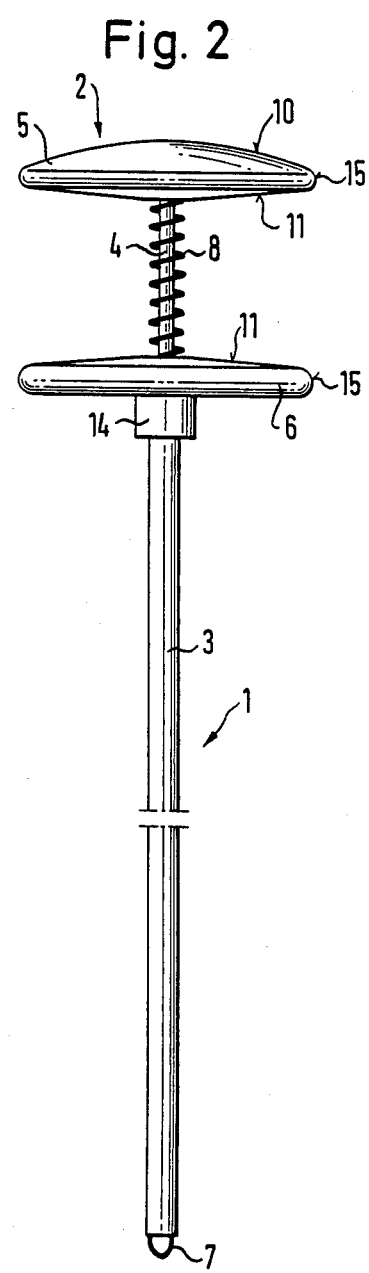

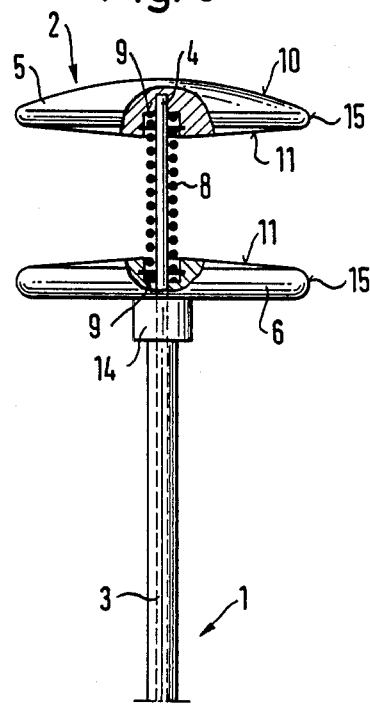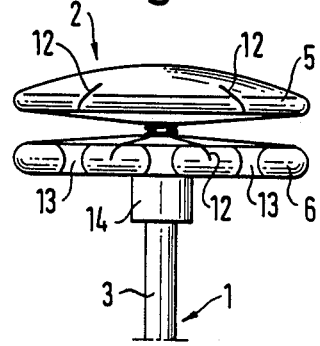

INSTRUMENT GRIP

The invention relates to an instrument grip for medical instruments.

Instrument grips or handles of the aforementioned type are adequately known in medicine for surgery and examinations. Independently of the field of use, such as e.g. laparoscopy or endoscopy, on the proximal side these instruments are equipped with two gripping members which, in the same way as scissors, have two ring-like gripping parts for operation by means of the fingers of one hand. For the axial displacement of the instrument shaft within the instrument sleeve, said gripping parts are moved towards or away from one another.

The aforementioned medical instruments have numerous different uses e.g. as medical forceps, particularly for removing tissue, sample excision, foreign body removal and the like.

However, it is a disadvantage of said medical instruments equipped with the known grip that frequently a rotary movement of the instrument shaft relative to the instrument sleeve is required during operations and examinations. This can become necessary if the surgeon recognizes, e.g. during myoma removal, that the corresponding tissue part can be excised in the best possible way if the instrument shaft and therefore also the distal-side gripping or cutting instrument is rotated by e.g. 180°. Thus, in such a case, the surgeon must follow this necessary rotation of 180° with his hand, so that specifically in the case of such manipulations which must be performed extremely carefully, completely unergonomic operating positions for the surgeon arise. Compared with the starting position for the aforementioned medical instrument, in the case of a 180° rotation, the instrument grip with the two ring-like gripping parts are oppositely positioned, i.e. so-to-speak "upside down".

On the basis of these disadvantages of the prior art, the problem of the present invention is to provide an instrument grip which, in the case of simple construction, meets the medical requirements and in particular permits a favourable and improved handling possibility during rotary movements of the medical instrument, specifically its shaft, when surgery is being performed on the patient.

A fundamental idea of the invention is to get away from the hitherto used ring-like gripping parts projecting on one side and asymmetrically from the instrument and instead of these to fit at least to the instrument shaft a gripping part, which is e.g. constructed centrosymmetrically to the shaft axis. In this basic configuration, the gripping part diameter should not exceed the size of the inner hand surface or palm. Thus, a relatively flat and disk-shaped gripping part can be moved axially with respect to the instrument sleeve by exerting pressure by means of the hand and in the circumferential or rotary direction by means of the finger or thumb.

By means of said inventive gripping disk it is possible for the surgeon, even during surgery, to bring the instrument fixed in non-rotary manner on the distal side to the instrument shaft easily and without giving up the basic position of the hand into any random rotary position by finger actuation. Thus, surgery can be performed in a much more optimum manner, because the distal-side instrument can assume any rotary position. However, the specific advantage for the surgeon is that said instrument grip permits an ergonomically sensible handling and avoids unusual or even "cramped" operating positions.

Although the main successful results with the instrument grip according to the invention are already obtained though the construction of the back gripping member on the axially displaceable and rotary instrument shaft in the form of a gripping disk, it is advantageous to also construct the gripping member of the instrument sleeve held in non-rotary manner during surgery as a flat gripping disk and appropriately both gripping members are constructed similarly and with the same diameter. The design of the front gripping member as a gripping disk provides a reliable possibility for the support and guidance of the distal-side surface of the gripping disk between the fingers.

The circular configuration of the gripping members also makes it possible during and after a rotary movement with the medical instrument to perform the same actuation as in the basic position. Appropriately markings in the form of depressions with a numerical indication or different configurations, such as width are provided for detecting the normal position of the instrument. The surgeon is consequently aware of the rotary position by means of the gripping disk without visually detecting the position of the distal instrument. Apart from a circular, discus-like design of the gripping disks, it is also possible to have orthogonal, elliptical or similar circumferential regions of the gripping members.

In the case of medical forceps or gripping instruments, e.g. biopsy forceps or atraumatic grippers, it is appropriate to forcewise pretension the gripping disk rigidly connected to the instrument shaft with respect to the front gripping disks, e.g. by means of a spring. In this embodiment the axial displaceability of the instrument shaft and optionally a spreading apart of the distal-side gripping instrument is possible by means of simply exerting pressure by the hand through the closing movement between fingers and palm. On reducing or removing this force, the instrument shaft and the distal-side gripping instrument are moved axially rearwards in the instrument sleeve. This force can solely be applied by the spring provided between the two gripping disks. However, this force can be intensified by inserting a finger between the gripping disks.

The arrangement of the spring between the gripping disks is such that the relative rotary movement of at least the gripping disk connected in non-rotary manner to the instrument shaft is possible in an unimpeded manner. For this purpose, one spring end can be axially fixed to a gripping disk, whereas the other spring end is axially secured on or in the other gripping disk. Apart from the aspect of easy operation of such medical instruments, obviously account must be taken of the fundamental criteria, such as easy dismantlability and fitability for sterilization or autoclaving of the instrument with corresponding material requirements.

The invention is described in greater detail hereinafter relative to two non-limitative embodiments and the attached drawings, wherein show:

FIG. 1 The longitudinal section through a medical instrument e.g. a gripper for laparoscopy or endoscopy, with gripping disks compressed in the axial direction, so that at the distal side a gripper is opened.

FIG. 2 The instrument according to FIG. 1 in an axial view in the inoperative position.

FIG. 3 An axial partial section through the gripping area of the instrument according to FIG. 2.

FIG. 4 An axial view of another embodiment of an instrument grip.

The medical instrument 1 shown in FIG. 1 essentially has an axially extending instrument sleeve 3, in which is axially movable and rotatable an instrument shaft 4. In the embodiment of FIG. 1, a gripper 7 is provided at the distal-side end of instrument shaft 4. This gripper 7 is spread apart in the position in which the gripping disk 5 engages on the gripping disk 6 rigidly connected to instrument sleeve 3.

In the embodiment according to FIG. 1, both gripping disks 5, 6 are roughly circular and relatively flat in the manner of a discus. The distal-side surface of the lower gripping disk 6 is kept flat and passes via a sleeve attachment 14 into instrument sleeve 3. The latter is rigidly connected to sleeve attachment 14 or gripping disk 6, which is rounded in the edge region.

The surface of gripping disk 5 remote from the instrument is curved in spherical manner, so that optimum gripping and engagement in the palm of the hand is possible.

In the embodiment according to FIG. 2, a spiral spring 8 is provided around instrument shaft 4 between the two gripping disks 5 and 6. The constructional arrangement of spiral spring 8 is such that a rotary movement of gripping disk 5 by at least 360° with respect to gripping disk 6 is just as possible as the axial displaceability of instrument shaft 4. However, in the axial direction, spring 8 is so fixed with the two gripping disks, that a further movement from the end or inoperative position (FIG. 2) is only possible by means of a spring extension.

When the medical instrument is in the end position, the distal-side gripping instrument 7 is closed forcewise and can in fact be drawn completely into instrument sleeve 3. The facing inner faces of gripping disks 5, 6 are provided with flat bevels 11 in the manner of frustums. In this configuration, even when the two gripping disks are compressed in the circumferential region, an engagement possibility for the fingers exists, so that the force exerted on the distal side, e.g. on the gripper can be intensified by a radial insertion of the thumb.

The partial section according to FIG. 3 shows the instrument grip, as in the example of FIGS. 1 and 2, in the inoperative position, in which the gripping disks 5 and 6 have a maximum spacing. In the facing inner faces of gripping disks 5, 6 is formed in each case a circular groove 9, in which guidewise engages the corresponding end of spiral spring 8. Spiral spring 8 can be rotary at both ends and preferably at at least one end.

The two ends of the spiral spring are so axially secured, e.g. by means of circlips engaging in the circular grooves, that there is a maximum spacing of the gripping disks in the inoperative position. The arrangement of the spiral spring 8 combined with the design of the spring and the circular grooves 9 is such that in the case of an engagement of the axial areas of gripping disks 5 and 6, the distal-side instrument is moved axially furthest out of the instrument sleeve 3. The fixing of spiral spring 8 with respect to the two gripping disks 5, 6 is such that it is possible to dismantle with a few manipulations for sterilization purposes.

FIG. 4 shows in the radial viewing direction an instrument grip 2 equipped with flat inner faces. Edge depressions 13, e.g. as milled-out portions are provided on the circumferential edge and permit an easier rotary movement of gripping disk 6 by means of one finger. A similar embodiment with edge depressions can also be used for gripping disk 5. According to FIG. 4, gripping disk 5 is equipped with one or more depressions 12, which represent locating marks for the starting or rotary position of gripping disk 5 with respect to gripping disk 6. The diameter of gripping disks 5, 6 is appropriately 5 to 6 cm.

I claim:

1. An instrument grip for medical forceps, said instrument grip comprising:
   two gripping members operable by one hand,
   an outer instrument sleeve and an inner instrument shaft movable relative to each other and each including a gripping member rigidly connected to the proximal ends of said outer instrument sleeve and said inner instrument shaft, respectively,
   said gripping members being spring-tensioned with respect to each other to ensure a maximum spacing of said gripping members in an operative position,
   said gripping members being constructed as gripping disks, said gripping disk of said instrument shaft, n operation, lies in the palm of the user while said gripping disk of said instrument sleeve is gripped by the fingers of the user,
   said gripping disk of said instrument shaft being freely rotatable by a finger over 360° relative to said outer instrument sleeve, and
   said gripping disks having a minimum axial spacing between radial edge regions so that a radial insertion of a finger between said gripping disks is possible during a relative reciprocal axial movement of said gripping members.

2. An instrument grip according to claim 1, wherein said gripping member of said instrument sleeve is constructed as a gripping disk.

3. An instrument grip according to claim 2, wherein said gripping members have substantially the same diameter.

4. An instrument grip according to claim 2, wherein said gripping members are circular.

5. An instrument grip according to claim 2, wherein said gripping members are constructed with edge depressions.

6. An instrument grip according to claim 2, wherein said gripping members are spring-pretensioned with respect to one another.

7. An instrument grip according to claim 6, wherein said spring pretension ensures a maximum spacing of the gripping members in the inoperative position.

8. An instrument grip according to claim 1, wherein said gripping member of said instrument shaft is curved on the proximal side.

9. An instrument grip according to claim 2, wherein said facing faces of said gripping member, considered in axial section, are constructed as a flat frustum, at least in an edge region, and includes a minimum spacing of said gripping members in a region of their longitudinal axis.

10. An instrument grip for medical forceps, said instrument grip comprising:
    two gripping members operable by one hand,
    an outer instrument sleeve and an inner instrument shaft movable relative to each other and each including a gripping member rigidly connected to the proximal ends of said outer instrument sleeve and said inner instrument shaft, respectively,
    said gripping members being spring-tensioned with respect to each other to ensure a maximum spacing of said gripping members in an inoperative position, said gripping members being constructed as gripping disks, said gripping disk of said instrument shaft, in operation, lies in the palm of the user while said gripping disk of said instrument sleeve is gripped by the fingers of the user, and said gripping disk of said instrument shaft being freely rotatable by a finger over 360° relative to said outer instrument sleeve.

11. An instrument grip according to claim 10, wherein said gripping disks include facing faces constructed as a flat frustrum considered in axial section and includes a minimum spacing of said gripping disks in a region of their longitudinal axis.

12. An instrument grip according to claim 10, wherein said gripping member of said instrument shaft is curved on the proximal side.

13. An instrument grip according to claim 10, wherein circumferential edges of said gripping members are rounded in axial section.

14. An instrument grip according to claim 11, wherein said gripping members are circular and have substantially the same diameter.

15. An instrument grip according to claim 10, wherein said gripping member of said instrument shaft has a marking in an edge region for a starting position and a rotation angle.

16. An instrument grip according to claim 10, wherein both gripping members have markings in an edge region for a starting position and a rotation angle relative to one another.

17. An instrument grip according to claim 10, wherein said gripping members include edge depressions.

18. An instrument grip according to claim 14, wherein a spring for tensioning of said gripping disks is arranged between said facing faces of said gripping disks.

* * * * *